United States Patent [19]

Saito et al.

[11] Patent Number: 5,105,454

[45] Date of Patent: Apr. 14, 1992

[54] METHOD FOR ESTIMATING THE PRESS FORMABILITY OF GALVANNEALED STEEL SHEETS BY X-RAY DIFFRACTION

[75] Inventors: Minoru Saito; Kazuaki Chohata; Yusuke Hirose; Toshiharu Kittaka; Takeshi Nagatani, all of Sakai, Japan

[73] Assignee: Nisshin Steel Co., Ltd., Tokyo, Japan

[21] Appl. No.: 619,002

[22] Filed: Nov. 28, 1990

[30] Foreign Application Priority Data

Nov. 30, 1989 [JP] Japan .................................. 1-308917

[51] Int. Cl.$^5$ ............................................. G01N 23/20
[52] U.S. Cl. ........................................ 378/71; 378/70; 378/72; 427/8; 427/433
[58] Field of Search ............... 378/71, 70, 73; 427/8, 427/35, 36, 433, 45.1

[56] References Cited

U.S. PATENT DOCUMENTS

| | | | |
|---|---|---|---|
| 4,064,437 | 12/1977 | Hirose et al. | 378/73 |
| 4,764,945 | 8/1988 | Abe | 378/71 |
| 4,895,736 | 1/1990 | Sommer et al. | 427/433 |
| 4,913,746 | 4/1990 | Marder et al. | 427/433 |

*Primary Examiner*—Janice A. Howell
*Assistant Examiner*—Kim-Kwok Chu

*Attorney, Agent, or Firm*—Fleit, Jacobson, Cohn, Price, Holman & Stern

[57] ABSTRACT

A method for estimating the press formability of galvannealed steel sheets provided, wherein: the values found by:

$$\frac{I(\gamma) - I_B(\gamma)}{I(\gamma)}, \text{ and}$$

$$\frac{I(\Gamma) - I_B(\Gamma)}{I(\Gamma)}$$

wherein
- $I(\gamma)$ = the total X-ray diffraction intensity of the $\gamma$ phase,
- $I(\Gamma)$ = the total X-ray diffraction intensity of the $\Gamma$ phase,
- $I_B(\gamma)$ = the background X-ray diffraction intensity of the $\gamma$ phase,
- $I(\gamma) - I_B(\gamma)$ = the true X-ray diffraction intensity of the $\gamma$ phase,
- $I(\Gamma) - I_B(\Gamma)$ = the true X-ray diffraction intensity of the $\Gamma$ phase,
- $\Gamma$ = the $\Gamma$ phase of an Fe-Zn intermetallic compound in coating of galvannealed steel sheet, and
- $\gamma$ = the $\gamma$ phase of the intermetallic compound, are used as an index to determine the press formability.

1 Claim, 3 Drawing Sheets

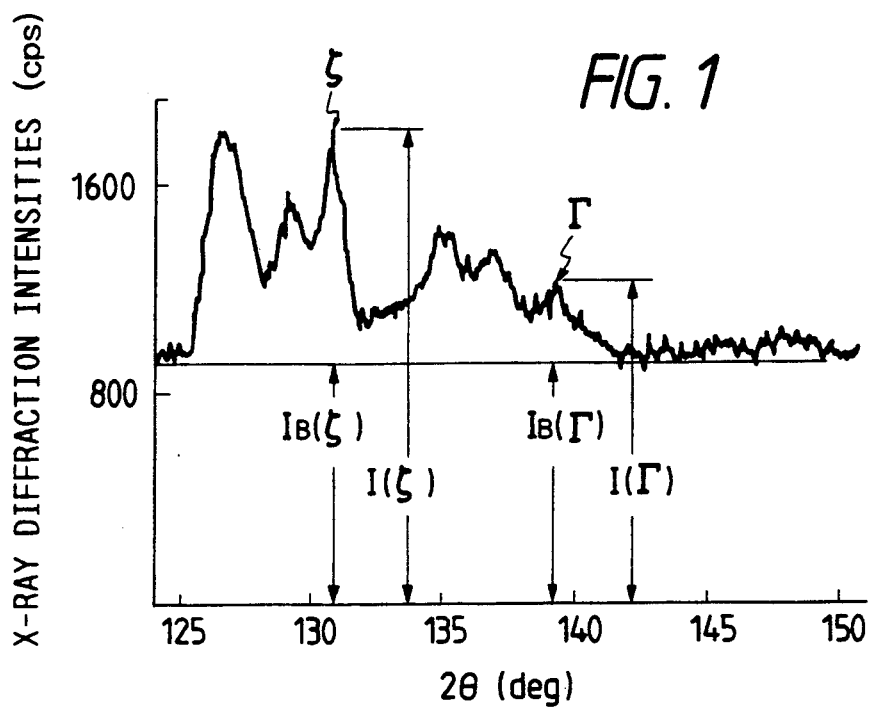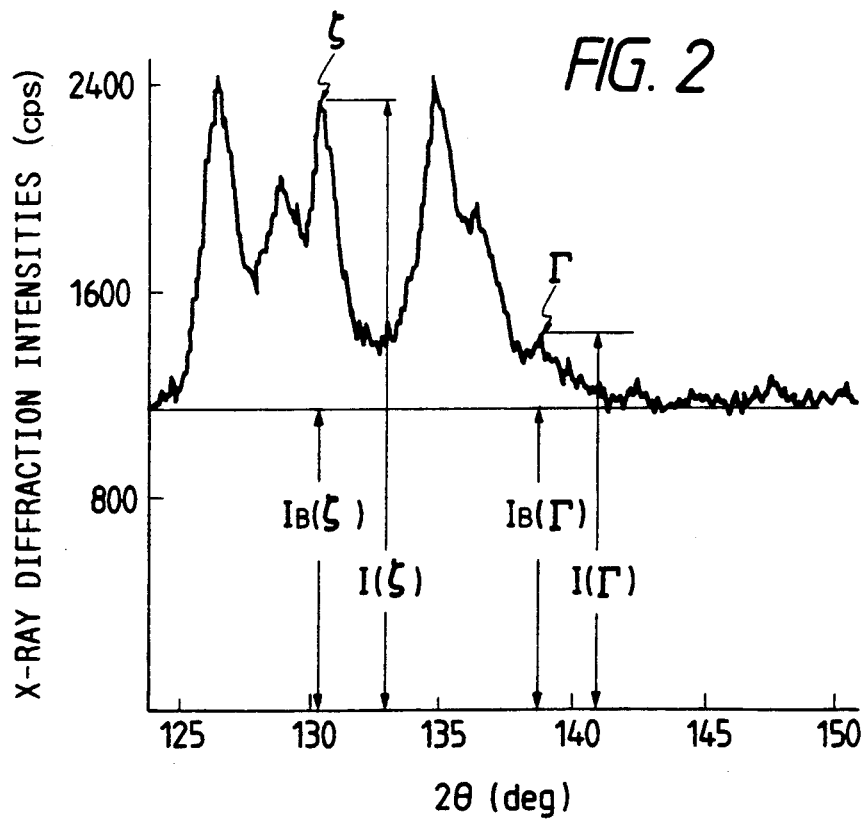

METHOD FOR ESTIMATING THE PRESS FORMABILITY OF GALVANNEALED STEEL SHEETS BY X-RAY DIFFRACTION

BACKGROUND OF THE INVENTION

1. Field of the Invention

The present invention relates to a method for estimating the press formability of galvannealed steel sheet by X-ray diffraction and, more particularly, to a method for making an estimation of whether or not galvannealed steel sheets produced by galvanizing and post-heat treatments can provide the excellent press formability, e.g., rustproof steel sheets for car bodies by X-ray diffraction in a non-destructive and continuous manner without being affected by the coating weight.

2. Prior Art

Galvannealed steel sheets having paintablility adhesion of coating, weldability and press formability in addition to the corrosion resistance of galvanized steel sheets have heretofore been produced and used in various industrial fields. Such galvannealed steel sheets are produced by subjecting steel sheets to hot dip galvanizing electro-galvanizing or vapor zinc depositing and then to post-heat treatments, thereby alloying the zinc coating and the steel matrix.

When steel sheets are heat-treated after zinc coating, $\gamma$, $\delta_1$ and $\Gamma$ phases represented by $FeZn_{13}$, $FeZn_7$ and $Fe_5Zn_{21}$, respectively, are successively formed by the interdiffusion of Fe and Zn with the progress of alloying. In the production of galvannealed steel sheets, the degree of alloying has so far been controlled with the average content of Fe in the coating. At the same time, the average content of Fe in the coating has also been used as an index to control the quality of the galvannealed steel sheets. This is premised on the assumption that the structures (distribution of each phase) of the coating having a close correlation with the quality correspond to the average content of Fe.

According to the inventors' studies so far made, it has been found that because the average content of Fe in the coating does not necessarily coincide with the structures of the coating, it is not possible to have the reasonable quality constantly by using the average content of Fe in the coating as an index. This will now be explained for steel sheets produced by vapor zinc depositing in vacuo and hot-dip galvanizing. After alloying, for instance, both steel sheets contain an average Fe content of 10%, but steel sheets obtained by hot-dip galvanizing includes, in addition to the major $\delta_1$ phase with the $\Gamma$ phase, a limited proportion of the $\gamma$ phase. On the other hand, the vapor zinc coated steel sheets include, in addition to the major $\delta_1$ phase without $\Gamma$ phase, a thick $\gamma$ phase. In another instance wherein galvannealed steel sheets are produced from titanium added and aluminium killed steel sheets by hot-dip galvanizing, there is indeed a difference in the thickness of the $\gamma$ or $\Gamma$ phase even at the same average content of Fe.

It is believed that these phenomena occur due to the fact that the alloying of Fe-Zn by heating proceeds on the basis of diffusion under non-equilibrium conditions. Thus, the structures of coating such as the thickness of the $\gamma$ or $\Gamma$ phase differ even at the same average content of Fe. In order to perform quality control using the average content of Fe in the coating as an index, it is required to have the types of base steel and the coating conditions under strictly identical control. Also, considerable difficulty is encountered in controlling the quality of a wide variety of galvannealed steel sheets. Problems with measuring the average content of Fe in coating by chemical analysis are that cutting of galvannealed steel sheets is required for sampling and so much time is required for analysis, and are that feeding back to the alloying treatment is delayed.

In order to meet a recent demand toward making car bodies greatly rustproof, galvannealed steel sheets have increasingly been used. In particular, materials for automotive rustproof steel sheets are now increasingly produced by press forming with severe drawing. From the results of studies so far made of the quality of galvannealed steel sheets and the structure of the coating, it has been found that the structures of the coating, in which a large amount of the $\gamma$ phase is present on the surface, offers a problem in connection with severe drawing, because the $\gamma$ phase, formed on the uppermost layer of galvannealed steel sheets, is relatively soft. In other words, it is preferred that the $\gamma$ phase is reduced as much as possible. This is because, in the case of galvannealed steel sheets with the coating structures in which a large amount of the $\gamma$ phase is present on the surface, it is so increased in the surface friction with a mold (or die) during drawing that its feeding into the mold gets worse, possibly resulting in the wall break of steel sheet or the sticking of the coating to the mold.

When a large amount of the $\Gamma$ phase grows with the progress of alloying while the $\gamma$ phase disappears from the surface of the coating, on the other hand, there occurs so-called a powdering phenomenon in which, because of the $\Gamma$ phase being hard but brittle, the coating layer peels off during press forming. When this powdering becomes vigorous, almost all of the coating layer falls away from the steel sheets, so that the corrosion resistance of the coating does not only deteriorate, but also affects adversely press formability.

Thus, the quantities of the $\gamma$ and $\Gamma$ phases in the coating have a close correlation with the quality, especially, press formability, of galvannealed steel sheets. In order to obtain galvannealed steel sheets with good press formability, the alloying conditions have to be regulated to ensure that the quantities of the $\gamma$ and $\Gamma$ phases grown does not exceed a proper value, estimating the drawability and anti-powdering property after alloying depending upon the purpose of use. Because the amount of the $\gamma$ phase remaining on the surface of the coating and the amount of the $\Gamma$ phase formed in the coating are unknown, aforesaid, usage of the average content of Fe in the coating as an index of degree of alloying is not possible to regulate the alloying conditions to improve press formability.

An object of this invention is therefore to solve the problems incidental to the index of degree of alloying so far used with the aforesaid technique. In order to make it possible to produce galvannealed steel sheets which are used not only for general purposes but also for severe press forming, a proper reference value for press formability is predetermined and, this is immediately fed back to a coating production line. In other words, the present invention has for its object to estimate the press formability of galvannealed steel sheets by using the aforesaid value as an index in a nondestructive and continuous manner without being affected by the coating weight, while the coating production line is running.

When a galvanized steel sheet is subjected to an alloying treatments, the $\gamma$, $\delta_1$ and $\Gamma$ phases grow successively after the η phase disappears from the surface of the coating. The proportion of the γ or Γ phase formed vary with other phases depending upon the degree of alloying. The inventors have examined the intensities of X-ray diffraction of the γ and Γ phases of each of various coating wherein the proportion of each phase differs depending upon the degree of alloying. In consequence, it has been found that the thickness or quantity of the γ and Γ phases corresponds to the total X-ray diffranction intensities I(γ) and I(Γ) of the γ and Γ phases. Further studies have revealed that:

$$\frac{I(\gamma) - I_B(\gamma)}{I(\gamma)}, \text{ and}$$

$$\frac{I(\Gamma) - I_B(\Gamma)}{I(\Gamma)}$$

wherein
- I(γ) = the total X-ray diffraction intensity of the γ phase,
- I(Γ) = the total X-ray diffraction intensity of the Γ phase,
- $I_B(\gamma)$ = the background X-ray diffraction intensity of the γ phase,
- I(γ) − $I_B(\gamma)$ = the true X-ray diffraction intensity, of the γ phase, and
- I(Γ) − $I_B(\Gamma)$ = the true X-ray diffraction intensity of the Γ phase, have a good correlation with the quality of a product; the former with the (outer diameter) ratio of the diameter of the disc before drawing to the diameter of the flange after drawing when the draw depth is kept constant in cup drawing test and the latter with the powdering amount in peeling test after bending and bending-back. The above-defined proportions, calculated from the X-ray diffraction intensities of the γ and Γ phases measurable on or apart from the coating production line, can be used as an index to estimate press formability, thereby attaining the aforesaid object.

More specifically, the present invention provides a method for estimating the press formability of galvannealed steel sheets, wherein:

$$\frac{I(\gamma) - I_B(\gamma)}{I(\gamma)}, \text{ and}$$

$$\frac{I(\Gamma) - I_B(\Gamma)}{I(\Gamma)}$$

wherein
- I(Γ) = the total X-ray diffraction intensity of the γ phase,
- I(Γ) = the total X-ray diffraction intensity of the Γ phase,
- $I_B(\gamma)$ = the background X-ray diffraction intensity of the γ phase,
- I(γ) − $I_B(\gamma)$ = the true X-ray diffraction intensity of the γ phase,
- I(Γ) − $I_B(\Gamma)$ = the true X-ray diffraction intensity of the Γ phase,
- Γ = the Γ phase of an Fe-Zn intermetallic compound in coating of galvannealed steel sheets, and
- γ = the γ phase of the intermetallic compound, are used as a index to determine press formability; the former being used to estimate drawability and the latter to estimate anti-powdering property.

BRIEF DESCRIPTION OF THE DRAWINGS

FIG. 1 is a chart obtained by plotting the X-ray diffraction intensities of an galvannealed steel sheet with a coating weight of 40.6 g/m² and an average Fe content of 8.81% against a diffraction angle of 2θ, wherein I(γ) is the total X-ray diffraction intensity of the γ phase; $I_B(\gamma)$ the background X-ray diffraction intensity of the γ phase; I(Γ) the total X-ray diffraction intensity of the Γ phase; and $I_B(\Gamma)$ the background X-ray diffraction intensity of the Γ phase, FIG. 2 is a chart obtained by plotting the X-ray diffraction intensities of an galvannealed steel sheet with a coating weight of 70.0 g/m² and an average Fe content of 8.61% against a diffraction angle of 2θ, wherein I(γ) is the total X-ray diffraction intensity of the γ phase; $I_B(\gamma)$ the background X-ray diffraction intensity of the γ phase; I(Γ) the total X-ray diffraction intensity of the Γ phase; and $I_B(\Gamma)$ the background X-ray diffraction intensity of the Γ phase.

DETAILED EXPLANATION OF THE INVENTION

The principle of the present method for estimating the press formability of galvannealed steel sheets will now be expained with reference to galvannealed steel sheets provided by hot-dip galvanizing.

Measured are the X-ray diffraction intensities I(γ) and I(Γ) of the γ and Γ phases interplanar spacings (d) of about 1.26 Å and about 1.22 Å, respectively, of the galvannealed steel sheets and the corresponding background X-ray diffraction intensities $I_B(\gamma)$ and $I_B(\Gamma)$, as illustrated in FIGS. 1 and 2. From the correlation between the reference values found by:

$$\frac{I(\gamma) - I_B(\gamma)}{I(\gamma)}, \text{ and}$$

$$\frac{I(\Gamma) - I_B(\Gamma)}{I(\Gamma)}$$

and the drawability and anti-powdering property of galvannealed steel sheet, it is noted that when the coating weight is 100 g/m² or less at which the intensity of X-ray diffraction is measurable, an increase in the reference values has correlation with the degradation of drawability and anti-powdering property irrespective of the coating weight. It is thus possible to determine the reference values corresponding to practically allowable press formability. The reason why the reference values has nothing to do with the coating weight is that the larger the coating weight, the higher the X-ray diffraction intensities I(γ) and I(Γ) of the γ and Γ phases, but the corresponding background X-ray diffraction intensities $I_B(\gamma)$ and $I_B(\Gamma)$ increase linearly in correlation with the coating weight. Without using the average content of Fe in the coating, which has so far been used as an index to the degree of alloying, it is thus possible to produce galvannealed steel sheets having press formability by determining $I(\gamma)$, $I(\Gamma)$, $I_B(\gamma)$ and $I_B(\Gamma)$ by X-ray diffraction and finding the reference values by:

$$\frac{I(\gamma) - I_B(\gamma)}{I(\gamma)}, \text{ and}$$

$$\frac{I(\Gamma) - I_B(\Gamma)}{I(\Gamma)}$$

whereby the alloying conditions are regulated within the given range preset as mentioned above. The present method may be applied to the alloying of galvanized steel sheets obtained by other processes as well.

Figure 5:
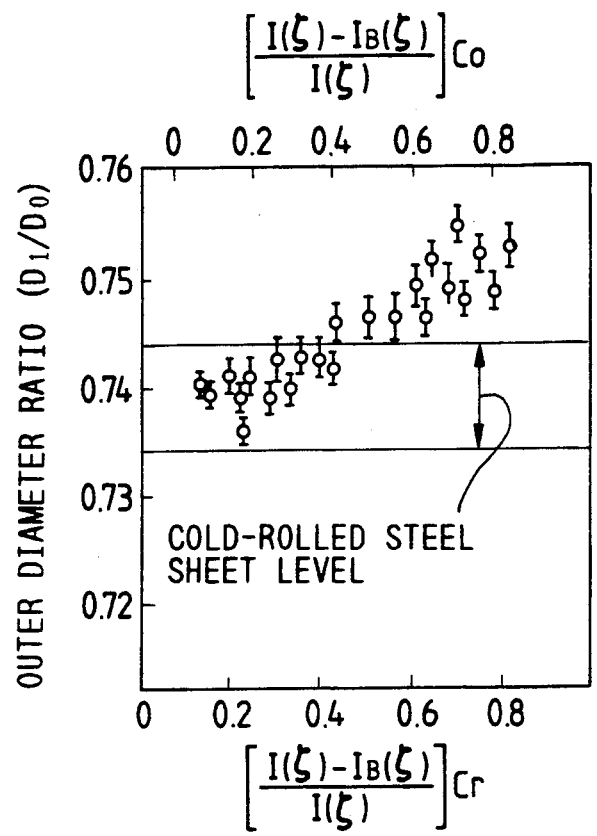
FIG. 5 is a chart expaining the correlation of the outer diameter ratio in cup drawing test with the reference values according to this invention, with the reference value using Co tube as the upper abscissa and using Cr tube as the lower abscissa.
Figure 6:
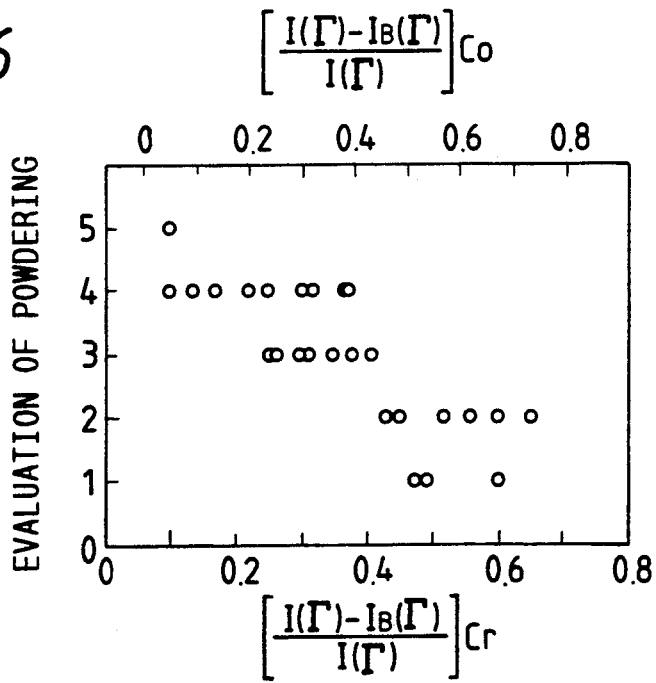
FIG. 6 is a chart explaining the correlation of the anti-powdering property in peeling test with the reference values according to this invention, with the reference value using Co tube as the upper abscissa and using Cr tube as the lower abscissa.

Even when the X-ray diffraction intensities $I(\gamma)$ and $I(\Gamma)$ of the $\gamma$ and $\Gamma$ phases are measured with interplanar spacing (d) taking a value other than about 1.26 Å and about 1.22 Å, or even when an X-ray tube other than a conventionally used Cr tube is used as the X-ray source, it has been ascertained that the reference values vary as shown in, e.g., FIGS. 5 and 6, but have correlation with press formability.

EXAMPLES

The method according to this invention will now be explained more illustratively but not exclusively with reference to Examples 1–7 and Comparative Examples 1–6.

The present method was applied to a production line for producing galvannealed steel sheets.

In this production line, the coating line was a continuous hot dipping line of a Sendzimir type of non oxygen furnace system, through which a 0.8 mm thick and 1,000 mm wide steel sheet containing Ti (C: 0.003%, Ti: 0.08%, Si: 0.016% and Mn: 0.14%) was fed at a line speed of 50 to 150 m per minute. For alloying treatment, an alloying furance was used, which includes a plurality of direct-flame burners located at positions corresponding to the edge and center positions of the front and back sides of the steel sheet, with the flow rates of combustion gases fed to the respective burners being independently controlled. In the respective examples and comparative examples, the coating weight was regulated by the adjustment of the flow rate of wiping gases through gas wiping equipment for blowing the gases to the steel sheets fed out of a coating metal in melting furnace.

The X-ray diffraction intensities were measured under the following conditions.

X-ray tube: Cr (optical parallel beam system)
Tube voltage and current: 40 KV and 70 mA
Solar slit: 0.6°.
Filter: V
Detector: Proportional counter
Interplanar spacings: about 1.26 Å for the $\gamma$ phase, about 1.22 Å for the $\Gamma$ phase For measuring the X-ray diffraction intensities, the measurement apparatus of alloying based on the present invention was repeatedly traversed widthwise over galvannealed steel sheets at the rate of one reciprocation a minute, during which measurements were taken at three points by every one way. From the thus measured X-ray diffraction intensities $I(\gamma)$ and $I(\Gamma)$ of the $\gamma$ and $\Gamma$ phases and the corresponding background X-ray diffraction intensities $I_B(\gamma)$ and $I_B(\Gamma)$, the reference values were found by:

$$\frac{I(\gamma) - I_B(\gamma)}{I(\gamma)}, \text{ and}$$

$$\frac{I(\Gamma) - I_B(\Gamma)}{I(\Gamma)}$$

and fed back to the alloying treatment to regulate a temperature in the alloying furnace, whereby the reference values were set at 0.3 or less to 0.40 or less inclusive for Examples 1–7, which were previously determined by measuring in galvannealed steel sheets with excellent drawability and anti-powdering property. In the compartive examples, the reference values applied departed from the above-defined range.

Figure 3:
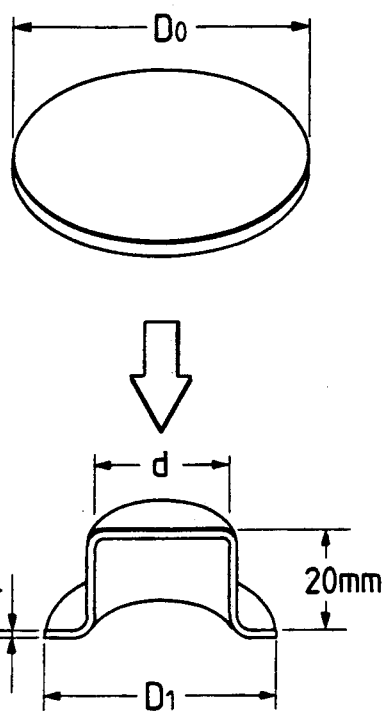
FIG. 3 is a view illustrating how to carry out in cup drawing test.
Figure 4:
FIG. 4 is a view illustrating how to perform in peeling test.

In each of the examples and comparaitve examples, 100 coils of galvannealed steel sheets, each of 2,000 m in length, were produced and test pieces were obtained from both edges and center positions of the top, middle and end regions of each coil. Drawability was estimated by the outer diameter ratios in cup drawing test, while anti-powdering property was evaluated by peeling tests of the coating after bending and bending-back. The cup drawing test was carried out under the conditions illustrated schematically in FIG. 3, using the same rustproof oil, while the peeling test was performed under the conditions illustrated schematically in FIG. 4.

Cup Drawing Tests

Test piece
Diameter of the disc before drawing (Do): 75 mm
Thickness of the steel sheet used for drawing: t mm
Mold
Diameter of the punch used for drawing (d): 40 mm
Radius of the end of the punch used for drawing: 5 mm
Radius of the shoulder of the punch used for drawing: 5t mm
Blank holder pressure during drawing: 1,000 kgf
State after testing
Depth of drawing: 20 mm
Diameter of the flange after drawing: $D_1$ mm

Peeling Tests

With the surface to be tested inside, the test piece was bent through 180° to form a curvature having a diameter six times as much as thickness of speciment t and, then, bent back. A cellophane adhesive tape was applied over the surface to be tested, and peeled off to visually observe the amount of powders deposited to the adhesive tape. Estimation was made by the following criteria:

5: No powders were found
4: Slight amount of deposition of powders were found
3: Some amount of deposition of powders were found
2: Considerable amount of deposition of powders were found
1: Without the application of the tape, a large amount of powders were found.

Ranks 5–3 offer no practical problem.
The results are reported in the following table.

TABLE

| Coating Weight (g/m²) | Reference values by X-Ray Diffraction ζPhase | Reference values by X-Ray Diffraction ΓPhase | Drawability (Outer Diameter Ratio) | Anti-powdering Property | Press Formability |
| --- | --- | --- | --- | --- | --- |
| Examples | | | | | |
| 1  30.2 | 0.21 | 0.37 | 0.735 | 4 | Good |
| 2  40.1 | 0.22 | 0.36 | 0.735 | 4 | Good |
| 3  42.5 | 0.30 | 0.35 | 0.739 | 3 | Good |
| 4  45.5 | 0.25 | 0.32 | 0.741 | 4 | Good |
| 5  58.5 | 0.32 | 0.25 | 0.742 | 3 | Good |
| 6  72.5 | 0.35 | 0.24 | 0.741 | 3 | Good |
| 7  89.1 | 0.33 | 0.24 | 0.742 | 3 | Good |
| Comparative Examples | | | | | |
| 1  29.8 | 0.15 | 0.60 | 0.740 | 2 | Inferior |
| 2  39.2 | 0.17 | 0.66 | 0.739 | 2 | Inferior |
| 3  48.1 | 0.65 | 0.25 | 0.751 | 4 | Inferior |
| 4  64.3 | 0.25 | 0.62 | 0.741 | 1 | Inferior |
| 5  65.2 | 0.70 | 0.21 | 0.754 | 4 | Inferior |
| 6  88.7 | 0.67 | 0.31 | 0.751 | 3 | Inferior |

From the results tabulated, it is found that in Examples 1-7 wherein alloying was carried out with the reference values within the above-defined range, almost all (precisely 99.9%) of the test pieces show "good" drawability and anti-powdering property. In Comparative Examples 1-6 wherein alloying was performed with reference values departing from the range of this invention, however, almost all (precisely 99.9%) of the test pieces show "inferior" drawability or anti-powdering property. Taken altogether, the comparative products are estimated to be "inferior".

According to the present method for estimating the press formability of galvannealed steel sheets for measuring by X-ray diffraction, the press formability of the galvannealed steel sheets produced by zinc coating and post-heat treatment (alloying treatment) can be estimated to use the reference values as an index found by:

$$\frac{I(\gamma) - I_B(\gamma)}{I(\gamma)}, \text{ and}$$

$$\frac{I(\Gamma) - I_B(\Gamma)}{I(\Gamma)}$$

Thus, it is possible to estimate press formability in a non-destructive and continuous manner and irrespective of a variation in the coating weight, during operation of the production line. By immediately feeding the reference values to the alloying conditions and control them under proper values, it is possible to produce uniformly and stably galvannealed steel sheets having with excellent press formability in longitudinal direction of coil. In consequence, any ongoing inspection can be dispensed with, leading to some advantages such as energy-saving and production cost reductions. With this invention, it is also easy to estimate the press formability of galvannealed steel sheets for a use excepting severe press forming. The present invention is thus of great industrial value.

What is claimed is:

1. A process for estimating the press formability of galvannealed steel sheets comprising the steps:
    providing a galvannealed steel sheet;
    applying an X-ray beam to a galvannealed surface of the steel sheet to produce X-ray diffractions;
    measuring the X-ray diffraction intensities of $\gamma$ and $\Gamma$ phases and background intensities of these phases;
    calculating a drawability reference value determined by:

$$\frac{I(\gamma) - I_B(\gamma)}{I(\gamma)}.$$

and calculating an anti-powdering reference value determined by:

$$\frac{I(\Gamma) - I_B(\Gamma)}{I(\Gamma)};$$

wherein
    $I(\gamma)$ = the total X-ray diffraction intensity of the $\gamma$ phase,
    $I(\Gamma)$ = the total X-ray diffraction intensity of the $\Gamma$ phase,
    $I_B(\gamma)$ = the background X-ray diffraction intensity of the $\gamma$ phase,
    $I(\gamma) - I_B(\gamma)$ = the true X-ray diffraction intensity of the $\gamma$ phase,
    $I(\Gamma) - I_B(\Gamma)$ = the true X-ray diffraction intensity of the $\Gamma$ phase,
    $\Gamma$ = the $\Gamma$ phase of an Fe-Zn intermetallic compound in coating of galvannealed steel sheet, and
    $\gamma$ = the $\gamma$ phase of the intermetallic compound; and
    determining press formability dependent on both the drawability and anti-powdering reference values.

2. A process for estimating the press formability of galvannealed steel sheet to produce sheets for severe press forming, comprising the steps:
    producing galvannealed steel sheet under controlled conditions some of which can be adjusted during production;
    applying an X-ray beam to the galvannealed surface of the steel sheet to produce diffractions;
    measuring the total and background X-ray diffraction intensity of $FeZn_{13}$ and $Fe_5Zn_{21}$ alloy phases on the coated surface of such galvanneal steel sheet;
    determining drawability reference values depending on such measured total and background X-ray diffraction intensities of only the $FeZn_{13}$ phase;
    determining anti-powdering reference values depending on such measured total and background X-ray diffraction intensities of only the $Fe_5Zn_{21}$ phase;
    comparing such drawability and anti-powdering reference values with empirically determined desired value ranges; and
    adjusting such controlled conditions during production depending on such comparisons to maintain the drawability and anti-powdering reference values within the desired value ranges.

3. The process of claim 2 in which the drawability reference value is determined by the steps:
    calculating a true X-ray diffraction intensity of the $FeZn_{13}$ phase by subtracting the background X-ray diffraction intensity of the $FeZn_{13}$ phase from the total X-ray diffraction intensity of the $FeZn_{13}$ phase; and
    calculating the drawability reference value by dividing the true X-ray diffraction intensity of the $FeZn_{13}$ phase by the total X-ray diffraction intensity of he $FeZn_{13}$ phase.

4. The process of claim 2 in which the anti-powdering reference value is determined by the steps:
    calculating a true X-ray diffraction intensity of the $Fe_5Zn_{21}$ phase of subtracting the background X-ray diffraction intensity of the $Fe_5Zn_{21}$ phase from the total X-ray diffraction intensity of the $Fe_5Zn_{21}$ phase; and calculating the drawability reference value by dividing the true X-ray diffraction intensity of the $Fe_5Zn_{21}$ phase by the total X-ray diffraction intensity of the $Fe_5Zn_{21}$ phase.

5. The process of claim 2 in which producing galvannealed steel sheet includes the steps:

feeding steel sheet moving through a galvanneal production line at a controlled rate;

depositing zinc for coating a surface of the sheet with zinc alloy of regulated coating weight; and annealing the coated steel sheet for a controlled time at a controlled temperature; and in which adjusting such controlled conditions during production to maintain the drawability and anti-powdering reference values within the desired ranges includes the step, adjusting the temperature of the annealing furnace depending on such comparisons.

6. The process of claim 1 further comprising the step:

press forming galvannealed steel sheets which are determined to have sufficient press formability.

* * * * *